(12) United States Patent
Summitt

(10) Patent No.: US 10,987,143 B2
(45) Date of Patent: Apr. 27, 2021

(54) FLEXIBLE SCREW

(71) Applicant: Conmed Corporation, Utica, NY (US)

(72) Inventor: Matthew C. Summitt, Palm Harbor, FL (US)

(73) Assignee: Conmed Corporation, Utica, NY (US)

( * ) Notice: Subject to any disclaimer, the term of this patent is extended or adjusted under 35 U.S.C. 154(b) by 121 days.

(21) Appl. No.: 16/000,164

(22) Filed: Jun. 5, 2018

(65) Prior Publication Data

US 2018/0344374 A1 Dec. 6, 2018

Related U.S. Application Data

(60) Provisional application No. 62/515,049, filed on Jun. 5, 2017.

(51) Int. Cl.
*A61B 17/86* (2006.01)
*A61B 17/88* (2006.01)

(52) U.S. Cl.
CPC ........ *A61B 17/8625* (2013.01); *A61B 17/863* (2013.01); *A61B 17/864* (2013.01); *A61B 17/8605* (2013.01); *A61B 17/8897* (2013.01)

(58) Field of Classification Search
CPC ............ A61B 17/7019; A61B 17/7026; A61B 17/7208; A61B 17/84; A61B 17/842; A61B 17/86; A61B 17/8605; A61B 17/8625; A61B 17/863; A61B 17/864
See application file for complete search history.

(56) References Cited

U.S. PATENT DOCUMENTS

| | | | | |
|---|---|---|---|---|
| 6,656,184 | B1 * | 12/2003 | White | A61B 17/8625 606/318 |
| 7,175,626 | B2 * | 2/2007 | Neff | A61B 17/7225 606/86 A |
| 7,662,173 | B2 * | 2/2010 | Cragg | A61B 17/70 606/279 |
| 7,833,256 | B2 * | 11/2010 | Biedermann | A61B 17/7004 606/300 |
| 8,690,917 | B2 * | 4/2014 | Suh | A61B 17/70 606/246 |
| 9,482,260 | B1 * | 11/2016 | Krause | F16B 35/041 |
| 2015/0374419 | A1 * | 12/2015 | Wolter | A61B 17/7059 606/71 |

(Continued)

*Primary Examiner* — Larry E Waggle, Jr.
(74) *Attorney, Agent, or Firm* — Bond, Schoeneck & King, PLLC; Frederick J.M. Price

(57) ABSTRACT

A flexible screw and method for non-rigid fixation between two bones. The flexible screw includes a head, and a body including a thread portion with a flexible shaft portion extending therebetween. The head has a diameter greater than that of the flexible shaft portion. The thread portion has a plurality of rigid threads while the flexible shaft portion has plurality of openings arranged in a pattern configuration. The openings extend at least partially through the flexible shaft portion. The flexible screw can be used for non-rigid fixation by inserting the thread portion in a first bone while the head is positioned on a distal side of an adjacent second bone. The flexible screw is tightened such that the flexible shaft portion extends in the joint between the first bone and the second bone. The flexible shaft portion provides stability while also adding back motility lost by the reduction in the size of the joint.

14 Claims, 2 Drawing Sheets

(56) References Cited

U.S. PATENT DOCUMENTS

2016/0038201 A1\* 2/2016 Cummings .......... A61B 17/866
 606/304
2017/0014170 A1 1/2017 Fallin et al.
2018/0092681 A1\* 4/2018 Lutz ................... A61B 17/8685

\* cited by examiner

FLEXIBLE SCREW

CROSS-REFERENCE TO RELATED APPLICATION

The present application relates and claims priority to U.S. Provisional Application No. 62/515,049 filed Jun. 5, 2017, the entirety of which is hereby incorporated by reference.

BACKGROUND OF THE INVENTION

1. Field of the Invention

The invention relates generally to anchors for bone fixation and more particularly, to a flexible screw for non-rigid fixation between two bones.

2. Description of Related Art

The syndesmosis joint is a meeting point of the fibula and the tibia in the leg above the ankle. The main functions of the syndesmosis joint are to provide stability and motility to the ankle joint and provide motility to the ankle joint. The most common cause of injury to the syndesmosis joint is a twisting or other rotational injury to the ankle. High ankle sprains in athletes are one example of injuries that cause damage to the syndesmosis joint.

After syndesmosis disruption of the ankle, the "gold standard" for repair is to place a syndesmosis screw between the fibula and the tibia above the ankle joint. However, as is virtually inevitable in all bone-to-bone fixation procedures, the size of the area between the adjacent bones is reduced. Similarly, in repairing syndesmosis disruption of the ankle, use of the syndesmosis screw results in a reduction of the syndesmosis joint. In addition, the rigidity of the traditional syndesmosis screw limits movement of the syndesmosis joint.

Therefore, there is a need for a bone screw that provides flexibility to a joint between two bones without compromising the stability of the fixation between the two bones.

SUMMARY OF THE INVENTION

The present invention is directed to, inter alia, a flexible screw and a method for non-rigid fixation between two bones. In one embodiment, the present invention is a flexible screw. The flexible screw includes a head and a body including a thread portion with a flexible shaft portion extending therebetween. The head has a first diameter, which is greater than a second diameter of the flexible shaft portion. The thread portion has a plurality of rigid threads thereon and the flexible shaft portion has plurality of openings arranged thereon in a pattern configuration. The openings extend at least partially through the flexible shaft portion.

In another embodiment, the present invention is a flexible screw system. The flexible screw system includes a flexible screw having a head and a body including a thread portion with a flexible shaft portion extending therebetween. The flexible screw has an inner volume extending therethrough. The flexible screw also has a plurality of rigid threads on the thread portion. The flexible shaft portion has a plurality of opening arranged thereon in a pattern configuration. The plurality of openings extends through the flexible shaft portion into the inner volume. The system also includes a guidewire configured for removable insertion within the inner volume.

In an alternative embodiment, the present invention is a method for non-rigid fixation between two bones. The method comprises the steps of: (i) providing a flexible screw having a head and a body including a thread portion with a flexible shaft portion extending therebetween, the head having a first diameter and the flexible shaft portion having a second diameter, wherein the first diameter is greater than the second diameter; a plurality of rigid threads on the thread portion; a plurality of openings arranged in a pattern configuration along the flexible shaft portion; and wherein the openings extend at least partially through the flexible shaft portion; (ii) inserting the thread portion into a first bone such that the head is positioned on a distal side of an adjacent second bone; (iii) positioning the flexible shaft portion in a joint between the first bone and the second bone; and (iv) tightening the flexible screw by advancing the thread portion into the first bone.

In accordance with any of the embodiments, the flexible shaft portion can be positioned anywhere along the body of the screw, and can exist as an intermittent portions between threaded portions.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
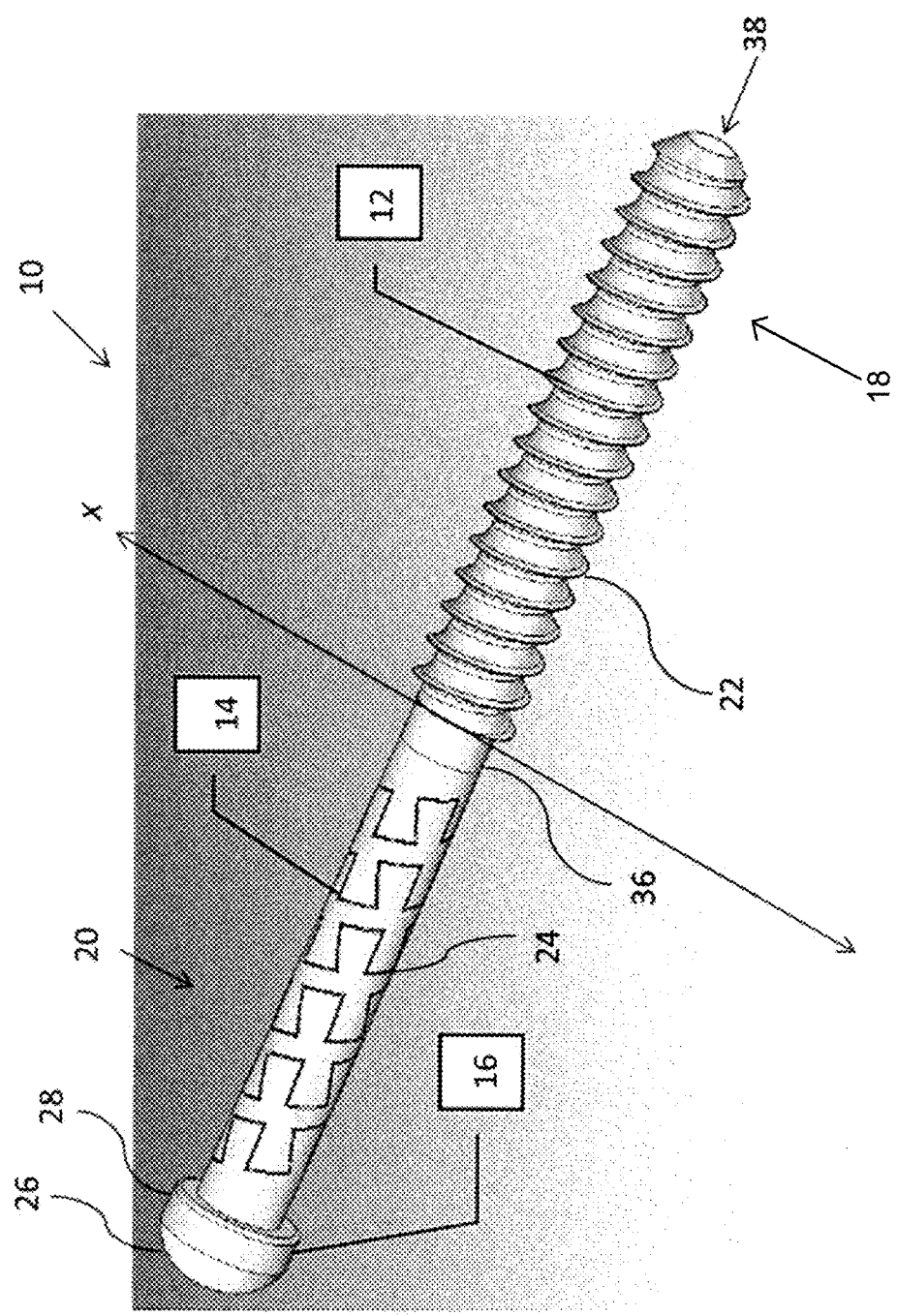
FIG. 1 is a perspective view of an illustrative embodiment of a flexible screw.

Referring now to FIG. 1, there is shown a perspective view of an illustrative embodiment of a flexible screw 10. The flexible screw 10 comprises a body including a thread portion 12 and a shaft portion 14, and a head 16. The thread portion 12 is at a first end 18 of the flexible screw 10 and the head 16 is on a second end 20 of the flexible screw 10. The shaft portion 14 extends between the thread portion 12 and the head 16, as shown in the embodiment in FIG. 1. In the depicted embodiment, the thread portion 12 comprises rigid threads 22 for anchoring the flexible screw to a bone. The rigid threads 22 of the thread portion 12 may be as rigid as conventional bone screws in order to provide a secure anchor point for the flexible screw 10.

To provide flexibility, the flexible screw 10 also comprises openings 24 in the shaft portion 14. In the depicted embodiment, the shaft portion 14 is approximately the same length as the thread portion 12; however, other proportions are contemplated for various surgical procedures. In the embodiment shown in FIG. 1, the openings 24 in the shaft portion 14 are thin laser cut slits. Also as shown, the openings 24 do not extend into an uncut portion 36 of the shaft portion 14, which connects the shaft portion 14 to the thread portion 12.

In addition, the openings 24 in FIG. 1, are arranged in a non-linear, patterned configuration. A pattern of thin openings 24 (i.e., slits) provides flexibility to the shaft portion 14 that could not be achieved if the openings 24 were large and spaced farther apart. The pattern of the openings 24 in FIG. 1 is a tooth-like or zipper pattern. However, any configuration of linear or non-linear patterns can be utilized for the openings 24 as may be appropriate to provide the preferred flexibility in a particular situation. In addition, FIG. 1 shows openings 24 in a pattern which extends at angle relative to a cross-sectional axis x of the flexible screw 10.

The openings 24 shown in FIG. 1 are laser cut; however, alternative methods for generating the openings 24 can be used (as should be understood by a person of ordinary skill in the art in conjunction with a review of this disclosure). In addition, the openings 24 may be extend entirely through the shaft portion 14 or extend only partially through the shaft portion 14. In one embodiment, the flexible screw 10 is cannulated such that the flexible screw 10 has a hollow inner volume 38. In the cannulated flexible screw 10, the openings 24 may extend through the shaft portion 14 to the inner volume 38.

Still referring to FIG. 1, the head 16 of the flexible screw 10 comprises a hemispherical cap 26 connected to a cylindrical end 28. The cylindrical end 28 connects the head 16 to the shaft portion 14. In the depicted embodiment, the diameter of the cylindrical end 28 is greater than the diameter of the shaft portion 14. The larger diameter of the cylindrical end 28 ensures that the flexible screw 10 is secured on the exterior (i.e., distal side) of an adjacent bone and will not pull through the hole created by the thread portion 12 of the flexible screw 10.

Figure 2:
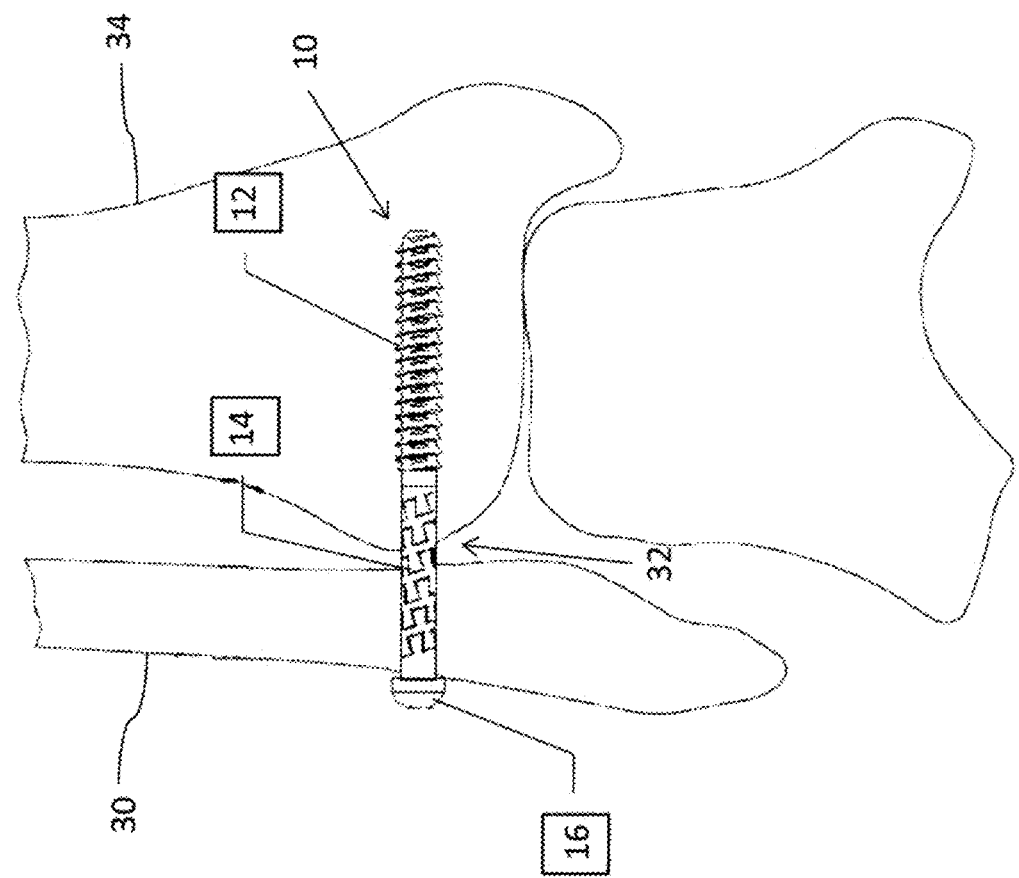
FIG. 2 is a schematic representation of an illustrative embodiment of a flexible screw secured between two bones.

Turning now to FIG. 2, there is shown a schematic representation of an illustrative embodiment of a flexible screw secured between two bones. In the depicted embodiment, the flexible screw 10 is inserted into the syndesmodic joint; however, the flexible screw 10 can be utilized in numerous other procedures requiring non-rigid fixation between two bones. First, to insert the flexible screw 10 into the surgical site, the flexible screw 10 can be cannulated such that it can be inserted over a guidewire (not shown) prior to use at the surgical site.

As shown in FIG. 2, the thread portion 12 is inserted through the fibula 30 and the syndesmodic joint 32 and into the tibia 34. Specifically, the thread portion 12 is inserted into the tibia 34 such that the shaft portion 14 is positioned in the syndesmodic joint 32 through the fibula 30. As shown, the head 16 of the flexible screw 10 is fixed or otherwise positioned against the exterior (i.e., lateral side or distal side) of the fibula. As the flexible screw 10 is tightened, the syndesmosis is reduced. However, due to the flexibility of the shaft portion 14, the syndesmodic joint 32 will still have some motility despite its reduced size. Further, although the shaft portion 10 is flexible, it still provides some resistance in the sagittal plane.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A flexible screw, comprising:
    a head, and a shaft body distally extending from the head and including a thread portion with a flexible shaft portion extending therebetween;
    wherein the head comprises a hemispherical cap with a proximal-most rounded end and a distal cylindrical end, the distal cylindrical end positioned between the proximal-most rounded end and a most proximal end of the shaft body;
    wherein the distal cylindrical end has a first diameter, and the most proximal end of the shaft body has a second diameter, wherein the first diameter is greater than the second diameter;
    a plurality of rigid threads positioned on the thread portion;
    a plurality of openings arranged in a pattern configuration along the flexible shaft portion; and
    wherein the openings extend at least partially through the flexible shaft portion.

2. The flexible screw of claim 1, wherein the openings are laser cut.

3. The flexible screw of claim 1, wherein the flexible shaft portion is cannulated such that the flexible shaft portion comprises an inner volume.

4. The flexible screw of claim 3, wherein the openings extend into the inner volume of the flexible shaft portion.

5. The flexible screw of claim 1, wherein the pattern is non-linear.

6. The flexible screw of claim 1, wherein the pattern extends at an angle from a cross-sectional axis of the flexible shaft portion.

7. The flexible screw of claim 1, wherein the flexible shaft portion is a first length and the thread portion is a second length, the first length being approximately equal to the second length.

8. A flexible screw system, comprising:
a head, and a shaft body distally extending from the head and including a thread portion with a flexible shaft portion extending therebetween;
wherein the head comprises a hemispherical cap with a proximal-most rounded end and a distal cylindrical end, the distal cylindrical end positioned between the proximal-most rounded end and a most proximal end of the shaft body;
wherein the distal cylindrical end has a first diameter, and the most proximal end of the shaft body has a second diameter, wherein the first diameter is greater than the second diameter;
an inner volume extending through the head, the thread portion, and the flexible shaft portion;
a plurality of rigid threads positioned on the thread portion;
a plurality of openings arranged in a pattern configuration along the flexible shaft portion, the plurality of openings extending through the flexible shaft portion into the inner volume; and
a guidewire configured for removable insertion within the inner volume.

9. The system of claim 8, further comprising an uncut portion of the flexible shaft portion connecting the flexible shaft portion to the thread portion.

10. The system of claim 8, wherein the pattern extends at an angle from a cross-sectional axis of the flexible shaft portion.

11. A method for non-rigid fixation between two bones, comprising the steps of:
providing a flexible screw having a head with a hemispherical cap comprising a proximal-most rounded end and a distal cylindrical end, and a shaft body distally extending from the head and including a thread portion with a flexible shaft portion extending therebetween, the distal cylindrical end positioned between the proximal-most rounded end and a most proximal end of the shaft body, wherein the distal cylindrical end has a first diameter, and the most proximal end of the shaft body has a second diameter, wherein the first diameter is greater than the second diameter; a plurality of rigid threads on the thread portion; a plurality of openings arranged in a pattern configuration along the flexible shaft portion; and wherein the openings extend at least partially through the flexible shaft portion;
inserting the thread portion into a first bone such that the head is positioned on a distal side of an adjacent second bone;
positioning the flexible shaft portion in a joint between the first bone and the second bone; and
tightening the flexible screw by advancing the thread portion into the first bone.

12. The method of claim 11, further comprising the steps of:
providing an inner volume extending through the head, the flexible shaft portion, and the thread portion; and
inserting a guidewire through the inner volume.

13. The method of claim 12, further comprising the step of advancing the flexible screw along the guidewire to the distal side of the second bone.

14. The method of claim 11, wherein the first bone is a tibia and the second bone is a fibula.

* * * * *